(12) United States Patent
Savolainen

(10) Patent No.: US 10,269,231 B2
(45) Date of Patent: Apr. 23, 2019

(54) SOUND GENERATION

(71) Applicant: Nokia Technologies Oy, Espoo (FI)

(72) Inventor: Teemu Savolainen, Nokia (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/763,785

(22) PCT Filed: Sep. 29, 2015

(86) PCT No.: PCT/FI2015/050645
§ 371 (c)(1),
(2) Date: Mar. 27, 2018

(87) PCT Pub. No.: WO2017/055675
PCT Pub. Date: Apr. 6, 2017

(65) Prior Publication Data
US 2018/0276970 A1    Sep. 27, 2018

(51) Int. Cl.
| G08B 21/18 | (2006.01) |
| G08B 3/10 | (2006.01) |
| G08B 21/02 | (2006.01) |
| A61B 5/00 | (2006.01) |

(52) U.S. Cl.
CPC .......... *G08B 21/182* (2013.01); *A61B 5/0002* (2013.01); *G08B 3/10* (2013.01); *G08B 21/02* (2013.01)

(58) Field of Classification Search
CPC ........ G08B 21/182; G08B 3/10; G08B 21/02; G08B 17/10; G08B 17/117; F25D 29/008; A61B 5/0002
USPC .................................................. 340/328, 521
See application file for complete search history.

(56) References Cited

U.S. PATENT DOCUMENTS

| 5,451,930 A | 9/1995 | McDaniel |
| 5,589,824 A | 12/1996 | Lynch |
| 5,801,633 A | 9/1998 | Soni |
| 7,113,610 B1 | 9/2006 | Chrysanthakopoulos |
| 7,461,394 B1 * | 12/2008 | Sano ........................ A63F 13/10 725/153 |
| 2014/0244710 A1 | 8/2014 | Sharma et al. |
| 2015/0029880 A1 | 1/2015 | Burns et al. |

FOREIGN PATENT DOCUMENTS

EP    0 666 702 A2    8/1995

OTHER PUBLICATIONS

International Search Report and Written Opinion received for corresponding Patent Cooperation Treaty Application No. PCT/FI2015/050645, dated Feb. 4, 2016, 13 pages.

(Continued)

*Primary Examiner* — Ali Neyzari
(74) *Attorney, Agent, or Firm* — Alston & Bird LLP

(57) ABSTRACT

A computing device or server receives statuses from devices in a network. The statuses may be determined according to sensor data relating to environmental characteristics, or vital signs of a person or animal. Sound data is generated according to the received statuses, and provided to a computing device, such as one in the vicinity of the devices. The computing device provides audio output reflecting the sound data, such that a user may passively monitor statuses of the devices. The sound data may be further varied according to the proximity of the computing device to the device with which the sound data is associated, indicating to the user which one of a plurality of devices the audio output relates.

20 Claims, 9 Drawing Sheets

(56) References Cited

OTHER PUBLICATIONS

Yan H. et al.: "Wireless sensor network based E-health system—implementation and experimental results", IEEE Trans. on Consumer Electronics, vol. 56 No. 4, Nov. 2010, pp. 2288-2295.

Lang W. et al.: "The 'Intelligent Container'—a cognitive sensor network for transport management", IEEE Sensors Journal, vol. 11 No. 3, Mar. 2011, pp. 688-698.

The Real and Virtual Internet of things—Session 4 | Max Marchant [Online] [retrieved Oct. 3, 2018]. Retrieved from the Internet: <URL: https://maxmarchant.wordpress.com/2015/01/30/the-real-and-virtual-internet-of-things-session-4/>. (Jan. 30, 2015) 2 pages.

Headset creates "3D soundscape" to help blind people navigate cities [online] [retrieved Oct. 3, 2018]. Retrieved from the Internet: <URL: https://www.dezeen.com/2014/11/06/future-cities-catapult-microsoft-guide-dogs-3d-heads . . . >. (dated Nov. 6, 2014) 15 pages.

Mesa Imaging AG—SwissRanger SR4000—miniature 3D time-of-flight range camera. 3D Camera [online] [retrieved Oct. 3, 2018]. Retrieved from the Internet: <URL: https://web.archive.org/web/20120102025203/http://www.mesa-imaging.ch/>. (Jan. 2, 2012) 1 page.

Audio Video Applications | Internet of Things. Think WiSmart [online] [retrieved May, 22, 2015]. Retrieved from the Internet: <URL: http;//www.econais.com/applications/audio-video-applications/>. (dated 2014) 4 pages.

Peltola, M., *Augmented Reality Audio Applications in Outdoor Use*, Master's Thesis, Helsinki University of Technology (Feb. 23, 2009) 66 pages.

\* cited by examiner (D)

(E)

(F)

(G)

200

```
┌─────────────────────────────────────────┐
│ Store respective sound information for   │
│ one or more resource types               │
│                                          │
│ 210                                      │
└─────────────────────────────────────────┘
                    │
                    ▼
┌─────────────────────────────────────────┐
│ Receive, from one or more accessory      │
│ devices 110, a respective time series    │
│ of resource values that indicates a      │
│ status of a resource available in the    │
│ respective accessory device              │
│                                          │
│ 220                                      │
└─────────────────────────────────────────┘
                    │
                    ▼
┌─────────────────────────────────────────┐
│ Generate, in dependence of resource      │
│ values in said one or more time series,  │
│ using said sound information for the     │
│ resource types available in said one or  │
│ more accessory devices 110, a sound      │
│ signal that is descriptive of the        │
│ statuses of said resources available in  │
│ said one or more accessory devices       │
│                                          │
│ 230                                      │
└─────────────────────────────────────────┘
```

Figure 11

SOUND GENERATION

RELATED APPLICATION

This application was originally filed as PCT Application No. PCT/FI2015/050645 filed Sep. 29, 2015.

TECHNICAL FIELD

Non-limiting example embodiments of the present invention relate to generating, at a device, a sound that is descriptive of operation of an accessory device that is connectable to the device via a local wireless link.

BACKGROUND

Using a local wireless link, such as a Bluetooth Basic Rate/Enhanced Data Rate (BT BR/EDR) link or a Bluetooth Low Energy (BLE) link, to connect a computing device such as a mobile phone, a tablet computer or a laptop computer to an accessory device such as speakers or to a printer has become a standard measure. Such local wireless links are equally applicable for connecting any computing device to accessories of different type, such as sensor devices that provide environmental information, home appliances and even industrial equipment or systems. In particular, the emerging Internet of Things (IoT) forms a framework that is estimated to introduce a vast number of accessory devices that are accessible by basically any computing device via a local wireless links.

One class of accessory devices that represent the IoT includes accessory devices that are arranged to provide sensory data. As an example, such sensory data may comprise e.g. environmental information obtained from a sensor that may be included in or coupled to the accessory device, and the sensor may be arranged to measure an environmental characteristic (such as ambient temperature, air pressure, air humidity, $CO_2$ level, etc.). As another example, the sensory data from the accessory device may comprise sensory information that is indicative of a vital sign of a person or an animal (such as temperature, pulse, respiratory rate, blood pressure, oxygen saturation, etc.).

In an environment that includes a high number of accessory devices that provide sensory data, the computing device may continuously receive a vast amount of information, only part of which carries meaningful information to a user or users of the computing device. Consequently, continuously providing the received information e.g. via a display of the computing device may result in an information overload that likely contributes the user(s) of the computing device to miss some important pieces of information. In particular, in case of sensory data that is descriptive of an environmental characteristic or a vital sign of a person or an animal, the user(s) may be primarily interested in detecting any out-of-the-ordinary piece of information (a change in air pressure, a change in heart rate) without constantly directing their full attention to the display screen.

SUMMARY

According to an example embodiment, a method is provided, the method comprising storing, in an apparatus, respective sound information for one or more resource types, the sound information for a resource type comprising sound data that defines one or more audio signals associated with the resource type and sound control data that defines use of the sound data for generation of a sound signal that is descriptive of a status of a resource that represents said resource type in dependence of one or more resource values that indicate the status of the resource; receiving, in the apparatus, from one or more accessory devices, a respective time series of resource values that indicates a status of a resource available in the respective accessory device; and generating, in the apparatus, in dependence of resource values in said one or more time series, using said sound information for the resource types available in said one or more accessory devices, a sound signal that is descriptive of the statuses of said resources available in said one or more accessory devices.

According to another example embodiment, an apparatus is provided, the apparatus comprising a communication portion comprising at least a communication apparatus for wireless communication with other apparatuses over a wireless link; and a control portion arranged to cause the apparatus to store respective sound information for one or more resource types, the sound information for a resource type comprising sound data that defines one or more audio signals associated with the resource type and sound control data that defines use of the sound data for generation of a sound signal that is descriptive of a status of a resource that represents said resource type in dependence of one or more resource values that indicate the status of the resource; receive, using said communication apparatus, from one or more accessory devices, a respective time series of resource values that indicates a status of a resource available in the respective accessory device; and generate, in dependence of resource values in said one or more time series, using said sound information for the resource types available in said one or more accessory devices, a sound signal that is descriptive of the statuses of said resources available in said one or more accessory devices.

According to another example embodiment, an apparatus is provided, the apparatus comprising a means for storing respective sound information for one or more resource types, the sound information for a resource type comprising sound data that defines one or more audio signals associated with the resource type and sound control data that defines use of the sound data for generation of a sound signal that is descriptive of a status of a resource that represents said resource type in dependence of one or more resource values that indicate the status of the resource; a means for receiving, from one or more accessory devices, a respective time series of resource values that indicates a status of a resource available in the respective accessory device; and a means for generating, in dependence of resource values in said one or more time series, using said sound information for the resource types available in said one or more accessory devices, a sound signal that is descriptive of the statuses of said resources available in said one or more accessory devices.

According to another example embodiment, a computer program is provided, the computer program comprising computer readable program code configured to cause performing at least the method according to the example embodiment described in the foregoing when said program code is executed on a computing apparatus:

The computer program according to an example embodiment may be embodied on a volatile or a non-volatile computer-readable record medium, for example as a computer program product comprising at least one computer readable non-transitory medium having program code stored thereon, the program which when executed by an apparatus cause the apparatus at least to perform the operations described hereinbefore for the computer program according to an example embodiment of the invention.

The exemplifying embodiments of the invention presented in this patent application are not to be interpreted to pose limitations to the applicability of the appended claims. The verb "to comprise" and its derivatives are used in this patent application as an open limitation that does not exclude the existence of also unrecited features. The features described hereinafter are mutually freely combinable unless explicitly stated otherwise.

Some features of the invention are set forth in the appended claims. Aspects of the invention, however, both as to its construction and its method of operation, together with additional objects and advantages thereof, will be best understood from the following description of some example embodiments when read in connection with the accompanying drawings.

BRIEF DESCRIPTION OF FIGURES

The embodiments of the invention are illustrated by way of example, and not by way of limitation, in the figures of the accompanying drawings, where FIG. 1 schematically illustrates some components of a communication arrangement according to an example embodiment;

FIG. 11 illustrates a method according to an example embodiment.

DESCRIPTION OF SOME EMBODIMENTS

Figure 1:
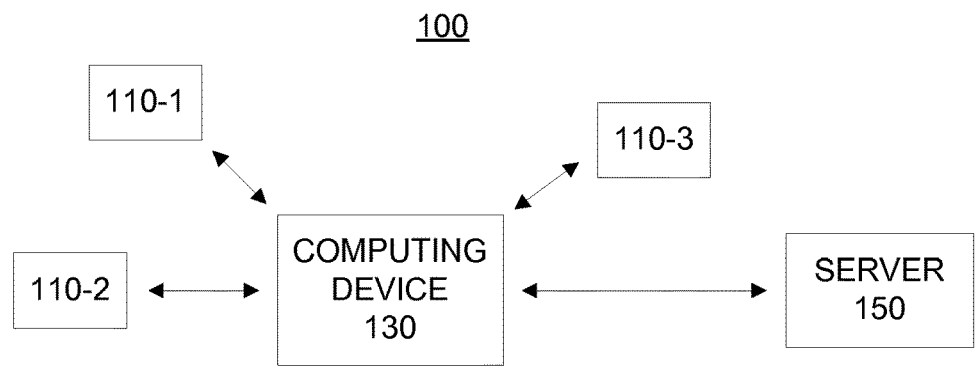

FIG. 1 schematically illustrates some components and/or entities of a communication arrangement 100 to depict an exemplifying framework for one or more embodiments of the present invention. The communication arrangement 100 comprises one or more accessory devices 110 (represented in FIG. 1 by accessory devices 110-1, 110-2 and 110-3), a computing device 130, and a server device 150. The communication arrangement 100 serves as a framework for generating a sound that is descriptive of current status of at least one of the one or more accessory devices 110. In the following, this text mostly refers to a single accessory device using the reference numeral 110 (without the suffix that identifies a specific instance of the accessory device, e.g. one of the accessory devices 110-1, 110-2 and 110-3) for improved editorial clarity in this regard.

The accessory device 110 is typically a special-purpose device for providing access to information and/or to a service. As a non-limiting example, the accessory device 110 may comprise a device that is arranged to provide access to sensory information, e.g. to environmental information (such as ambient temperature, air pressure, air humidity, $CO_2$ level, etc.) or to information that is indicative of a vital sign of a person or an animal (such as temperature, pulse, respiratory rate, blood pressure, oxygen saturation, etc.), obtained from a respective sensor included in or coupled to the accessory device 110. The information, e.g. sensory information, may be available from the accessory device 110 via a communication interface, which may provide e.g. an interface for obtaining information from or via the accessory device 110, an interface for transferring information to or via the accessory device 110, and/or an interface for controlling operation of the accessory device 110 or operation of a device coupled thereto. As a specific example, the accessory device 110 may be a device that is part of the Internet of Things (IoT), in other words the accessory device may comprise an IoT device. Accessing or controlling the accessory device 110 via the communication interface will be described with more detailed examples later in this text.

The computing device 130 is equipped with audio processing means and audio output means or the computing device 130 is connectable to one or more devices that jointly provide the computing device 130 with access to audio processing means and audio output means. As an example, the audio output means may comprise one or more loudspeakers included in the computing device 130, one or more loudspeakers that are connected to the computing device 130, or headphones or a headset that are connected to the computing device 130. In case the audio output means is not included in the computing device 130 (i.e. in case the audio output means is connected or connectable to the computing device 130), the connection between computing device 130 and the audio output means may be provided by wired or wireless communication means. Various aspects pertaining to the audio processing and audio output under control of the computing device 130 will be described with more detailed examples later in this text.

According to an example, the computing device 130 is provided as a portable user device that is typically frequently carried by the user, such as a mobile phone, a smartphone, a portable gaming device, a portable music player or media player, a portable navigation device, a personal digital assistant (PDA), a tablet computer, etc. According to another example, the computing device 130 is provided as a semi-stationary device, i.e. a device that is basically a portable device but that is not typically moved from its location, that is only infrequently relocated from one place to another and/or that is used within a restricted geographical area (such as an office or home), such as a desktop computer, a laptop computer, a tablet computer, a fixed router, a mobile router, a base station of a cellular system (e.g. such as a microcell, a picocell or a femtocell), etc. According to a further example, the computing device 130 is provided as an accessory device such as headphones or a headset.

The server device 150 is typically a remote server device that is arranged to provide a server function that is accessible by a number of computing devices 110. Although described herein, for editorial clarity of description, as a single entity, the server function described herein by using the server device 150 as an example may be jointly provided by a number of server devices that are arranged to provide a cloud service or a cloud server arrangement.

Figure 2:
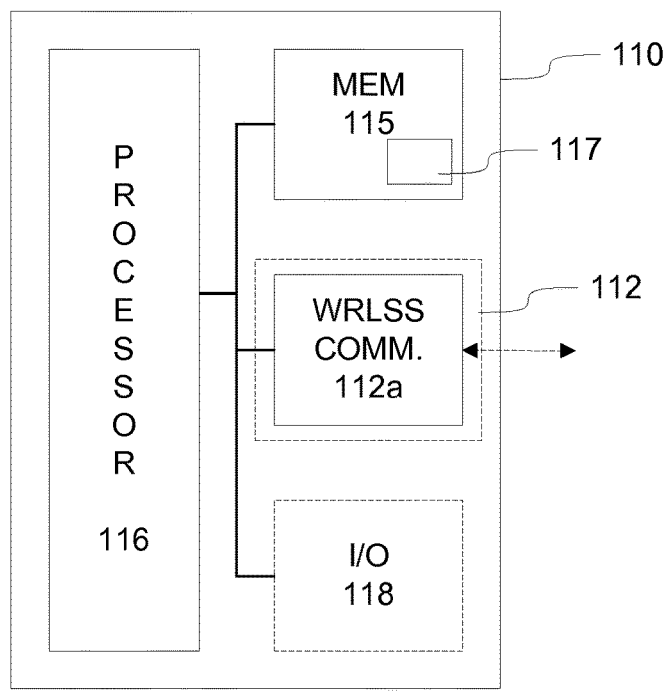
FIG. 2 schematically illustrates some components of a device according to an example embodiment.

FIG. 2 schematically illustrates some components of an exemplifying accessory device 110. The accessory device 110 may comprise further components or portions in addition to those depicted in FIG. 2, whereas the ones depicted therein are ones that are considered relevant for description of some embodiments of the present invention. The accessory device 110 comprises a communication portion 112 for wireless and/or wired communication with other devices. The communication portion 112 comprises at least a wireless communication apparatus 112*a*, whereas the communication portion 112 may comprise one or more further (wireless and/or wired) communication apparatuses. The wireless communication apparatus 112*a* may enable, for example, wireless communication with other devices by using a wireless communication technique or protocol that enables a point-to-point or a point-to-multipoint wireless connection with another device. The accessory device 110 is hence capable of communicating with other devices that are equipped with a wireless communication apparatus using the same technique/protocol, e.g. with the computing device 130.

The accessory device 110 further comprises a processor 116 and a memory 115 for storing data and computer program code 117. The accessory device 110 may further comprise user I/O (input/output) components 118 that may be arranged, possibly together with the processor 116 and a portion of the computer program code 117, to provide a user interface for receiving input from a user of the first device 110 and/or providing output to the user of the accessory device 110. The user I/O components 118 may comprise hardware components such as a display, a touchscreen, a touchpad, a mouse, a keyboard, and/or an arrangement of one or more keys or buttons, etc. The user I/O components 118 may be also referred to as peripherals. The processor 116 may be arranged to control operation of the accessory device 110 e.g. in accordance with a portion of the computer program code 117 stored in the memory 115 and possibly further in accordance with the user input received via the user I/O components 118 and/or in accordance with information received via the communication portion 112. The memory 115 and a portion of the computer program code 117 stored therein may be further arranged to, with the processor 116, to provide a control function for controlling operation of a communication apparatus of the communication portion 112, possibly together with a control portion or a control function that may be provided within the respective communication apparatus of the communication portion 112 (which will be described later in this text). These control functions may be, separately or jointly, referred to as control means (of the accessory device 110).

Figure 3:
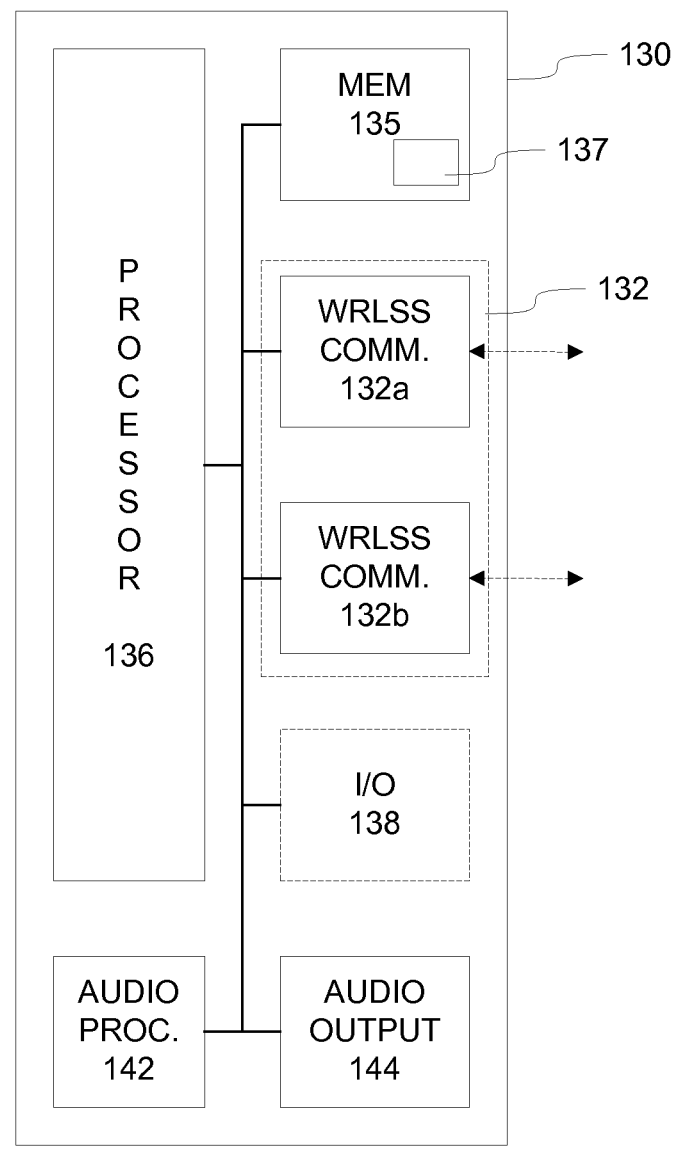
FIG. 3 schematically illustrates some components of a device according to an example embodiment.

FIG. 3 schematically illustrates some components of an exemplifying computing device 130. The computing device 130 may comprise further components or portions in addition to those depicted in FIG. 3, whereas the ones depicted therein are ones that are considered relevant for description of some embodiments of the present invention. The computing device 130 comprises a communication portion 132. The communication portion 132 comprises at least a first wireless communication apparatus 132*a* and a second communication apparatus 132*b*. The communication portion 132 may comprise one or more further (wireless and/or wired) communication apparatuses. The first wireless communication apparatus 132*a* is preferably one that enables wireless communication with the wireless communication apparatus 112*a*, thereby enabling the computing device 130 to wirelessly communicate with the accessory device 110 and/or with other devices equipped with communication apparatus using the same technique/protocol. The second communication apparatus 132*b* may comprise a wireless communication apparatus that applies a communication technique/protocol different from that of the wireless communication apparatus 132*a* or the second communication apparatus 132*b* may comprise a wired communication apparatus, and it may enable communication with the server device 150.

The computing device 130 further comprises a processor 136 and a memory 135 for storing data and computer program code 137. The computing device 130 may further comprise user I/O (input/output) components 138 that may be arranged, together with the processor 136 and a portion of the computer program code 137, to provide a user interface for receiving input from a user of the computing device 130 and/or providing output to the user of the computing device 130. The user I/O components 138 may comprise hardware components such as a display, a touchscreen, a touchpad, a mouse, a keyboard and/or an arrangement of one or more keys or buttons, etc. The user I/O components 138 may be also referred to as peripherals. The processor 136 may be arranged to control operation of the computing device 130 in accordance with a portion of the computer program code 137 stored in the memory 135 and possibly further in accordance with the user input received via the user I/O components 138 and/or in accordance with information received via the communication portion 132. The memory 135 and a portion of the computer program code 137 stored therein may be further arranged, with the processor 136, to provide a control function for controlling operation of a communication apparatus of the communication portion 132, possibly together with a control portion or a control function that may be provided within the respective communication apparatus of the communication portion 132 (which will be described later in this text). These control functions may be, separately or jointly, referred to as control means (of the computing device 130).

The computing device 130 further comprises an audio processing means 142 for processing audio and/or sound signals and an audio output means 144 for playing back sound signals. The audio processing means 142 may be arranged to provide one or more audio processing functions, example of which will be described in more detail later in this text. The audio output means 144 may comprise, for example, one or more loudspeakers. The example of FIG. 3 depicts the audio processing means 142 as a dedicated component of the computing device 130. In another example, the audio processing means 142 may be provided by software means, e.g. by a portion of the computer program code 137 that may be arranged, with the processor 136, to provide the one or more audio processing functions.

Figure 4:
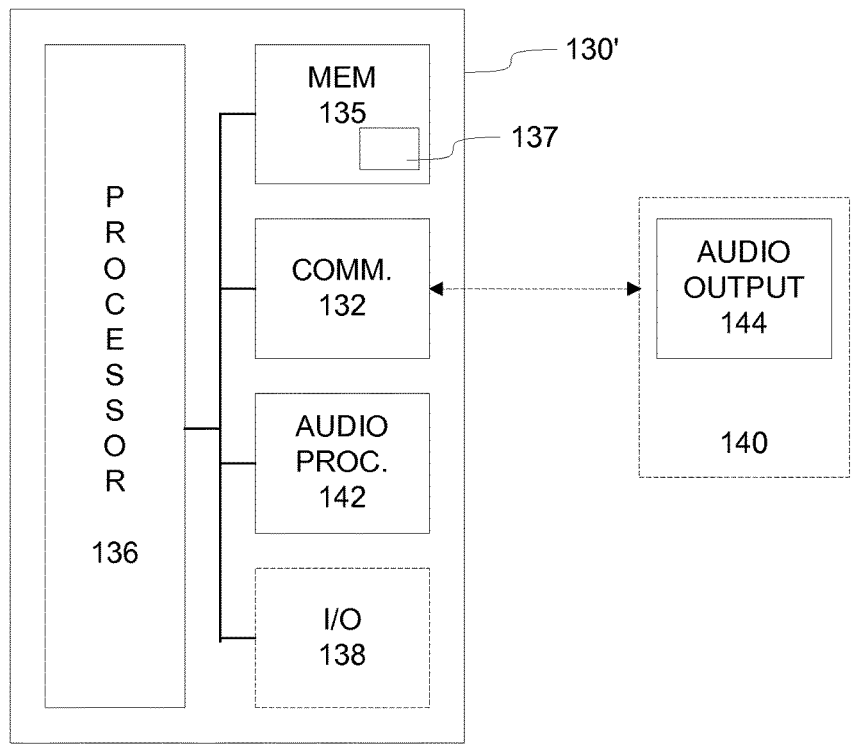
FIG. 4 schematically illustrates some components of a device according to an example embodiment.

FIG. 4 schematically illustrates some components of another exemplifying computing device 130', which is a variation of the computing device 130 described in the foregoing. The difference to the computing device 130 is that in the computing device 130' the audio output means 144 is provided in a separate audio accessory device 140, while the description provided in the foregoing applies for the other depicted components of the computing device 130'. The audio accessory device 140 may comprise e.g. a headset, headphones, a loudspeaker or an arrangement of two or more loudspeakers. The computing device 130' may be connectable to the audio accessory via the wireless communication apparatus 132*b* or via another wired or wireless communication apparatus of the communication portion 132. In another exemplifying variation of the computing device the audio processing means 142 is shared between the computing device and the audio accessory device 140 such that the computing device 130 comprises a first audio processing means that provides a first set of one or more audio processing functions and the audio accessory device 140 comprises a second audio processing means that provides a second set of one or more audio processing functions. In yet another exemplifying variation of the computing device 130, both the audio processing means 142 and the audio output means are provided in the audio accessory device 140 instead of providing them in the computing device 130. The computing device 130' (or other variants where the audio output means is provided outside the computing device 130) may be considered to serve as a gateway device or to provide a gateway function for facilitating generation of the sound that is descriptive of current status of at least one of the one more accessory devices 110.

Figure 5:
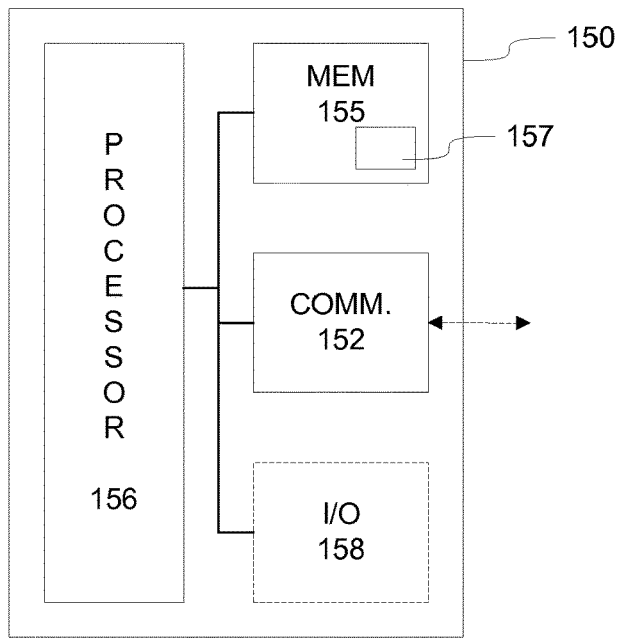
FIG. 5 schematically illustrates some components of a device according to an example embodiment.

FIG. 5 schematically illustrates some components of an exemplifying server device 150. The server device 150 may comprise further components or portions in addition to those depicted in FIG. 5, whereas the ones depicted therein are ones that are considered relevant for description of some embodiments of the present invention. The server device 150 comprises a communication portion 152. The communication portion 152 comprises at least a (wired or wireless) communication apparatus that enables communication with the computing device 130.

The server device 150 further comprises a processor 156 and a memory 155 for storing data and computer program code 157. The server device 150 may further comprise user I/O (input/output) components 158 that may be arranged, together with the processor 156 and a portion of the computer program code 157, to provide a user interface for receiving input from a user of the server device 150 and/or providing output to the user of the server device 150. The user I/O components 158 may comprise hardware components such as a display, a touchscreen, a touchpad, a mouse, a keyboard and/or an arrangement of one or more keys or buttons, etc. The user I/O components 158 may be also referred to as peripherals. The processor 156 may be arranged to control operation of the server device 150 in accordance with a portion of the computer program code 157 stored in the memory 155 and possibly further in accordance with the user input received via the user I/O components 158 and/or in accordance with information received via the communication portion 152. The memory 155 and a portion of the computer program code 157 stored therein may be further arranged, with the processor 156, to provide a control function for controlling operation of a communication apparatus of the communication portion 152, possibly together with a control portion or a control function that may be provided within the respective communication apparatus of the communication portion 152 (which will be described later in this text). These control functions may be, separately or jointly, referred to as control means (of the server device 150).

In the foregoing, the description refers to (wireless or wired) communication apparatuses of the communication portions 112, 132 and 152. Any of these communication apparatuses may be also considered as a respective communication means.

As described in the foregoing, the communication portions 112, 132, 152 may comprise e.g. respective wireless communication apparatuses 112a, 132a, 132b, and 152b, where a wireless communication apparatus 112a, 132a, 132b, 152b may be also referred to as a respective wireless communication means. A wireless communication apparatus may be provided e.g. as a respective chipset and/or as a respective communication module. For clarity and brevity of description, each of the wireless communication apparatuses 112a, 132a, 132b and 152b may be considered as a respective single logical entity that may also be capable of processing at least some of the information received via the wireless link and/or at least some of the information that is to be transmitted via the wireless link without external control from other components of the respective device 110, 130, 150 (e.g. from the processor 116, 136, 156, respectively). In an embodiment, a wireless communication apparatus 112a, 132a, 132b, 152b comprises e.g. a respective wireless transceiver portion for wireless communication and a respective control portion (or a control function) for controlling operation of the respective wireless transceiver portion and for processing information received/transmitted via the respective wireless transceiver portion. Such a control function may be provided by hardware means, by software means or by a combination of hardware means and software means. As an example in this regard, a wireless communication apparatus may comprise a memory, a processor and a portion of a computer program code stored in the memory may be arranged to, with the processor, provide the control function for controlling operation of the respective wireless communication apparatus 112a, 132a, 132b, 152b, either independently or jointly with the control function provided by the respective memory 115, 135, 155, a portion of the respective computer program 117, 137, 157 and the respective processor 116, 136, 156 of the respective device 110, 130, 150.

The wireless link between the wireless communication apparatus 112a and the wireless communication apparatus 132a (i.e. the wireless link between the accessory device 110 and the computing device 130) may be provided by employing a suitable short-range wireless communication technique or protocol. Such a wireless link may also be referred to as a local wireless link. The term short-range wireless communication as used herein refers to a wireless communication technique or protocol that enables typical operating range in the scale of tens of meters, e.g. up to 100 meters. However, especially in an indoor environment, the operating range of such short-range wireless communication technique/protocol may be significantly shorter e.g. due to walls and other stationary structures as well as furniture etc. that are likely to partially block or interfere with the radio communication between wireless communication portions 112a and 132a. On the other hand, in favorable conditions in outdoor use the operating range may extend to several hundreds of meters.

Examples of such a wireless technique/protocol include the Bluetooth Basic Rate/Enhanced Data Rate (BT BR/EDR) protocol and the Bluetooth Low Energy (BLE) protocol, both specified e.g. in the Bluetooth Specification Version 4.1, Covered Core Package version: 4.1 (publication date 3 Dec. 2013), incorporated herein by reference in its entirety. In the following, this document is referred to as a Bluetooth Specification. A further example of such a wireless technique/protocol is Wireless Local Area Network (WLAN) technology specified e.g. in IEEE 802.11 specifications (where the acronym IEEE stands for the Institute of Electrical and Electronics Engineers). However, the BT BR/EDR, BLE and WLAN technologies serve as illustrative and non-limiting examples in this regard, and the description generalizes into any short-range wireless communication technique/protocol.

The communication apparatus 132b, if provided as a wireless communication apparatus, may be arranged to employ any suitable wireless access technology known in the art to establish a connection to a computer network that further connects the computing device 130 to the server device 150. As an example in this regard, the wireless communication apparatus 132b may be arranged to employ the WLAN technology referred to in the foregoing to establish a wireless link with a wireless access point in its vicinity, which wireless link enables the computing device 130 to access a computer network that further enables connection to the server device 150. As another example, if provided as a wireless communication apparatus, the communication apparatus 132b may be arranged to employ a cellular access technology known in the art to establish a wireless link with a base station of a cellular network, which wireless link enables the computing device 130 to access a computer network that further enables connection to the server device 150. Instead of using wireless access, the communication apparatus 132b may employ a suitable wired technology known in the art, such as the Ethernet, in communicating with the computer network that further connects it to the server device 150. Similar considerations apply also to the communication apparatus 152b that enables the sever device 150 to connect the computing device 130 via the network.

In the following, this text may simply refer to a device 110, 130, 150 carrying out a certain operation (e.g. receiving and/or transmitting certain information and/or message(s)) when describing the act of a communication apparatus of the respective communication portion 112, 132, 152 carrying out said certain operation under control of the respective control function or control means. In particular, transfer of information or messages between the accessory device 110 and the computing device 130 is carried out via the wireless communication apparatuses 112a and 132a, unless explicitly stated otherwise; and transfer of information or messages between the computing device 130 and the server device 150 is carried out via the communication apparatus 132b, unless explicitly stated otherwise; and This approach is believed to improve editorial clarity and readability of the text, while the technical meaning of such expressions remains clear.

Figure 6:
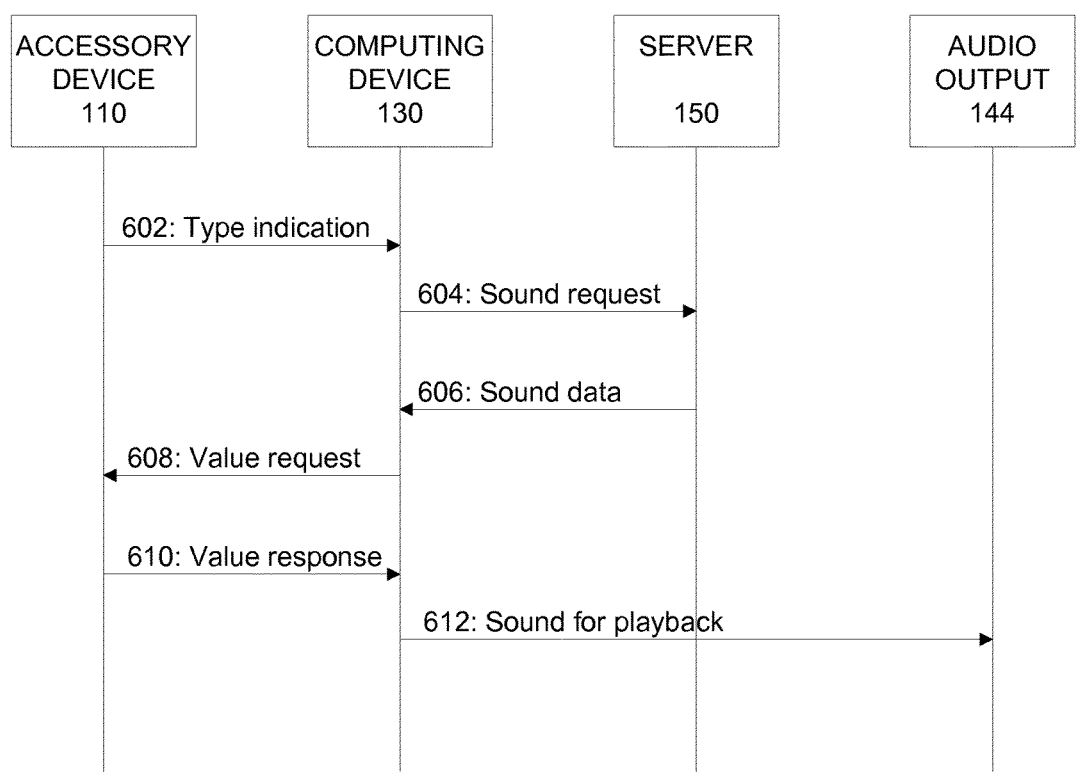
FIG. 6 depicts an example of signaling between elements of the communication arrangement according to an example embodiment.

FIG. 6 depicts a signaling chart that serves as an example of operation of the communication arrangement 100 at a high level. In particular, the illustrative and non-limiting example of FIG. 6 shows an outline of communication between the accessory device 110, the computing device 130 and the server device 150 for generation of a sound to be played back via the audio output means 144.

In step 602, the computing device 130 receives a resource type indication from the accessory device 110. The resource type indication serves to identify the resource or service available from or via the accessory device 110. The resource type indication typically indicates one of predefined resources or services, e.g. such that a plurality of predefined resource or service types each have a respective value of a resource type identifier assigned therefor, and the resource type indication carries the value of the resource type identifier assigned for the resource or service available in or via the accessory device 110. Examples of resource or service types include environmental information such as ambient temperature, air pressure, air humidity, etc. or medical information such as body temperature, pulse, respiratory rate, blood pressure, oxygen saturation, etc.

The resource type indication may be received in one or more messages transmitted from the accessory device 110, the one or more messages thereby serving at least to identify the resource or service available in or via the accessory device 110. Such messages may be referred to as resource discovery messages or service discovery messages. In case an accessory device 110 provides access to a plurality (e.g. two or more) resources or services, a resource discovery message (or a service discovery message) transmitted therefrom may carry resource type indications for two or more of the available services. In another example, separate resource discovery messages (or service discovery messages) are provided for each of the resources or services available in the accessory device 110.

The resource discovery message(s) may further comprise one or more identifiers or indications in addition to the resource type indication(s). As an example in this regard, the resource discovery message(s) may comprise a device identity indication. In such a case, the resource discovery message(s) further serve to identify the accessory device 110, thereby enabling other devices to discover and/or identify the accessory device 110 on basis of one or more resource discovery messages received therefrom. The device identity indication carries a device identifier assigned for the accessory device 110, and it may be referred to as an accessory device identifier. The accessory device identifier serves to uniquely identify the accessory device 110, and it may comprise e.g. an address, a serial number or other identifier assigned for the accessory device 110 or for the wireless communication apparatus 112a therein. As an example, an applicable address in this regard may be the device address of the wireless communication apparatus 112a.

Moreover, the resource discovery messages may further serve to carry connection information that is related to connection creation and connection establishment with the accessory device 110. Without losing generality, resource discovery messages that carry the connection information may be also referred to as device discovery messages. Consequently, other devices may be able to establish a connection with the accessory device 110 using the connection information received in the one or more device discovery messages, which connection may be employed to provide a communication interface that enables requesting and/or receiving, form the accessory device 110, information pertaining to the resource or service available in or via the accessory device 110. Device discovery messages may comprise advertising messages transmitted from the accessory device 110 on its own initiative (e.g. in accordance with a predefined schedule) or device discovery messages may comprise response messages transmitted from the accessory device 110 in response to a request received from the computing device 130.

The communication between the computing device 130 and the accessory device 110 may employ one or more communication protocols or one or more communication frameworks known in the art, configured such that it facilitates provision of the communication interface between the computing device 130 and the accessory device 110. Protocols used in providing the communication interface between the accessory device 110 and the computing device 130 may include, for example, one or more of the following: the Bluetooth Generic Attribute Profile (GATT), the Constrained Application Protocol (CoAP), the Hypertext Transfer Protocol (HTTP), the MQ Telemetry Transport (MQTT).

In step 604, the computing device 130 transmits an accessory sound request to the server device 150. The accessory sound request may be transmitted in response to discovering presence of a resource/service and/or an accessory device of interest. Assuming that an accessory device 110-k provides a resource of interest and hence such discovery may comprise discovering presence of the accessory device 110-$k$ and, further, determining that the discovered accessory device 110-$k$ provides a resource/service of interest and/or that the accessory device 110-$k$ is an accessory device 110 of interest.

In an example, the computing device 130 may consider presence of an accessory device 110-$k$ to be discovered in response to receiving at least one resource discovery message (or device discovery message) from the accessory device 110-$k$. In another example the computing device 130 may consider presence of an accessory device 110-$k$ to be discovered in response to receiving at least a predefined number of resource discovery messages (or device discovery messages) from the accessory device 110-$k$ within a predefined time period.

In a further example, the computing device 130 may consider presence of an accessory device 110-$k$ to be discovered in response to detecting the accessory device 110-$k$ to be sufficiently close to the computing device 130. In this regard, the computing device 130 may compute a received signal strength indication (RSSI) on basis of respective signals that carried one or more received resource discovery messages (or device discovery messages) and detect based on the computed RSSI whether the accessory device 110-$k$ is in close proximity to the computing device 130. As an example, such detection may comprise detecting the accessory device 110-$k$ to be in close proximity in response to the computed RSSI exceeding a predetermined threshold value and detecting the accessory device 110-$k$ not to be in close proximity in response to the RSSI not exceeding the predetermined threshold value.

As an example, determining that a discovered accessory device 110-$k$ provides a resource/service of interest and/or is an accessory device 110 of interest may comprise receiving, in one or more resource discovery messages (or device discovery messages) a resource type identifier that indicates one of one or more predefined resources or services of interest. In another example, the determination may comprise receiving, in one or more resource discovery messages (or device discovery messages) from the same accessory device 110, a resource type identifier and an accessory device identifier that jointly indicate one of one or more predefined pairs of a resource/service and an accessory device 110, i.e. jointly indicate a certain type of a resource or service to be available in a certain accessory device. In a further example, the determination may comprise receiving, in one or more resource discovery messages (or device discovery messages) an accessory device identifier that indicates one of one or more predefined accessory devices 110 of interest. In such a case the computing device 130 may store (e.g. in the memory 135 and/or a mass storage device accessible by the computing device 130) mapping information that defines, for one or more predefined accessory device identifiers, the respective resource type identifier that may be used in an accessory sound request to be transmitted to the server device 150.

Assuming, as an example, that accessory devices 110 that provide the resources of interest are recognizable in the computing device 130 on basis of received resource type identifiers, the computing device 130 may store (e.g. in the memory 135 and/or a mass storage device accessibly by the computing device 130) an accessory information database or a data structure of other type that includes one or more database entries. In this example, each of the database entries includes at least a data element storing a resource type identifier assigned for the respective resource types of interest. These resource type identifiers may comprise pre-stored data that has been received from a user via the user interface of the computing device 130 and stored in the accessory information database for subsequent use in discovery of a resource type and/or an accessory device 110 of interest.

In response to discovering presence of an accessory device 110-$k$ on basis of one or more resource discovery messages (or device discovery messages) received from an accessory device 110-$k$, the computing device 130 may search the accessory information database in an attempt to identify a database entry that stores a resource type identifier matching that received in the resource type indication from the accessory device 110-$k$. In case a database entry including a matching resource type identifier is found, the computing device 130 proceeds to transmit the accessory sound request to the server device 150. Furthermore, the computing device 130 may store the accessory device identifier received from the accessory device 110-$k$ (e.g. as an additional data element of the database entry found to include the matching resource type identifier) to indicate that the accessory device 110-$k$ is found to provide the respective resource or service of interest. In case a database entry including a matching resource type identifies is not found, no accessory sound request is transmitted in response to the resource discovery message (or device discovery message) from the accessory device 110-$k$.

In another example, the accessory information database stores one or more database entries that each include at least a data element that stores an accessory device identifier assigned for a respective accessory device 110 of interest, and the database search is carried out in an attempt to identify a database entry that stores an accessory device identifier matching that received from the accessory device 110-$k$. In a further example, the accessory information database stores one or more database entries that each include at least a data element that stores a pair of resource type identifier and an accessory device identifier that define a resource or service of interest available in an accessory device of interest. Consequently, the database search carried out in an attempt to identify a database entry that stores the identifiers matching those received in respective indications from the accessory device 110-$k$.

The accessory sound request comprises at least the resource type identification that includes the resource type identifier assigned for the resource or service type for which the sound information is requested, e.g. the resource type identifier received in one or more resource discovery messages from the accessory device 110-$k$ that provides the resource/service of interest. The accessory sound request may be transferred in one or more sound information request messages transmitted from the computing device 130 to the server device 150.

The communication between the computing device 130 and the server device 150 may employ one or more communication protocols or one or more communication frameworks known in the art, configured such that it facilitates provision of the accessory sound request to the server device 150 and accessory sound data, transmitted from the server device 150 in response to the accessory sound request, to the computing device 130. Protocols used in providing the communication interface between the accessory device 110 and the computing device 130 may include, for example, one or more of the following: Internet Protocol (IP), IP version 6 (IPv6), CoAP, HTTP, MQTT.

Instead of directly proceeding to transmitting the accessory sound request to the server device 150 (in step 604), the computing device 130 may determine, in response to discovering presence of a resource/service and/or an accessory device of interest, whether it already has accessory sound information associated with the resource or service available in or via the accessory device 110-k: in case the required accessory sound information as already available in the computing device 130, it may employ this information in generating the sound signal that is descriptive of the status of the resource or service available in or via the accessory device 110-k (thereby omitting steps 604 and 606), whereas in case the required accessory sound information is not available in the computing device 130, it may proceed into transmitting the accessory sound request in step 604.

The server device 150 may store (e.g. in the memory 155 and/or in a mass storage device accessible by the server device 150) an accessory sound database that includes one or more database entries. According to an example, each of the database entries represents one resource or service type and includes a respective data element at least for the following pieces of information:
- a resource type identifier that identifies the resource or service type represented by the database entry,
- accessory sound data that defines one or more sounds associated with the resource or service type represented by the database entry, and
- accessory sound control data that defines use of the one or more sounds of this database entry.

In response to the accessory sound request from the computing device 130, the server 150 device may search the accessory sound database in an attempt to identify a database entry that stores a resource type identifier matching that received in the accessory sound request from the computing device 130. In case a database entry including a matching resource type identifier is identified, the server device 150 proceeds to transmit accessory sound information to the computing device 130, as indicated in step 606. The accessory sound information comprises at least the accessory sound data and the accessory sound control data available in the identified database entry of the accessory sound database. In case a database entry including a matching resource type identifies is not found, the server device 150 may transmit an indication in this regard to the computing device 130 or it may simply ignore the accessory sound request without further action.

Upon reception, the computing device 130 stores the accessory sound data and the accessory sound control data received from the server device 150 for subsequent use. In this regard, the computing device 130 may arrange the received sound data in a local accessory sound database that may have a structure similar to that described in the forgoing in context of the accessory sound database of the server device 150. With such database structure the computing device 130 is able to identify and access the accessory sound data pertaining to the accessory device 110-k by identifying a database entry of the local accessory sound database that includes the resource type indicator assigned for the resource or service available in or via the accessory device 110-k. The local accessory sound database may be stored in the memory 135 or in a mass storage device accessible by the computing device 130.

The computing device 130 may employ a predefined communication interface to request and receive resource data from the accessory device 110-k. The communication interface hence provides communication procedures of communication functions that enable the computing device 130 at least to request resource data from the accessory device 110-k and to receive resource data from the accessory device 110-k. The communication interface may be provided by software means, e.g. as program code stored in the computing device 130 (e.g. a portion of the computer program code 137) that, when executed by the processor 136, causes the computing device 130 to implement the communication interface. As another example, the communication interface may be defined by a set of one or more rules, instructions, configurations, parameters or attribute values of a predefined communication framework such that it implements the communication interface. As an example in this regard, in context of BLE communication between the computing device 130 and the accessory device 110-k such communication framework may be provided in context of the GATT.

In step 608, the computing device 130 transmits a resource data request (or a resource value request) to the accessory device 110-k that has been discovered earlier to access the resource or service of interest therein. The resource data request may include a resource type indication that carries the resource type identifier to explicitly indicate the resource type for which resource data is requested. Instead of requesting resource data for a certain resource in the accessory device 110-k (by transmitting a respective resource type identifier in the resource type indication), the resource data request may constitute a request for resource data for all resources available in the accessory device 110-k, e.g. by including in the resource type indication (instead of a resource type value of interest) a predefined value that serves as an indication in this regard. The resource data request may be provided in one or more resource data request messages, transmitted from the computing device 130 to the accessory device 110-k. A resource data request message may comprise a resource data request for one or more resources available in the accessory device 110-k. In response to the resource data request, in step 610 the accessory device 110-k transmits resource data response to the computing device 130. The resource data response may be provided in one or more resource data response messages that carry the requested resource data, transmitted from the accessory device 110-k to the computing device 130. A resource data response message may comprise a resource type indication that carries the resource type identifier to explicitly indicate the resource type to which the resource response data carried in the message is associated. Alternatively, the resource data response messages may carry an accessory device identifier that may define, via the mapping information referred to in the foregoing, the respective resource type identifier.

As an example, the resource data available from and/or derivable in the accessory device 110-k may comprise a time series of resource values, where each resource value indicates the instantaneous value or status of the resource or service available in the accessory device 110-k. The accessory device 110-k may periodically produce a new or updated resource value (for a given resource available therein) that hence constitute the time series. Typically, but not necessarily, the accessory device provides a new/updated resource value at predefined time intervals (in other words, at a predefined frequency). The employed time interval may depend, for example, on characteristics of the accessory device 110-k and/or characteristics of the resource type available therein. The resource values may comprise, for example, numerical values, such as numbers that are indicative of instantaneous value of a temperature, a pressure, a pulse, etc. Hence, the resource values typically, but not necessarily, comprise measurement values from a sensor that is arranged to measure a predefined environmental characteristic or a predefined vital sign of a person or animal.

According to an example, the accessory device 110-*k* may respond to each resource data request by transmitting a single resource data response to the requesting computing device 130. The resource data response may comprise a single resource value or a sequence of resource values, where the sequence comprises a predefined or requested number of resource values or where the sequence covers a time period of predefined or requested duration. The requested number or requested duration may be specified in the resource data request transmitted from the computing device 130 to the accessory device 110-*k*. Consequently, the computing device 130 may send the resource data requests periodically (e.g. at predefined or user-definable intervals) in order to receive a corresponding sequence of resource data responses from the accessory device 110-*k*.

In another example, a resource data request received from the computing device 130 may trigger periodic transmission of resource data responses from the accessory device 110-*k*, for example, for a predefined time period, for a time period specified in the resource data request transmitted from the computing device 130 or until receiving, from the computing device 130, a request to terminate transmission of the resource data responses. The periodical transmission may involve the accessory device 110-*k* transmitting a resource data response f at predefined or requested intervals, and each resource data response may include a single resource value or a sequence of resource values, as described above.

Although depicted in the example of FIG. 6 as a step that occurs only after reception of the accessory sound data from the server data in step 606, in other examples the computing device 130 may alternatively transmit the (first) resource data request before reception of the accessory sound data from the server device 150 (e.g. between steps 604 and 606) or even before sending the accessory sound request to the server device 150 (e.g. between steps 602 and 604).

In response to or in the course of reception of the resource values (in the resource data responses) from the accessory device 110-*k*, the computing device 130 employs the audio processing means 142 to generate, in dependence of received resource values, a sound signal that is descriptive of the status of the resource available in or via the accessory device 110-*k* The computing device 130 provides the generated sound signal for playback in the audio output device 144, as indicated in step 612. Some examples of the sound signal generation are described by examples in the following.

The accessory sound data (stored in the accessory sound database in the server device 150 and) received from the server device 150 may define or comprise one or more audio signals. These audio signals may be provided as one more or sets of audio signals, such that one of the sets is pre-selected for subsequent generation of the sound signal in the computing device 130. Each set may define different version(s) of the audio signal(s) that is (are) intended to signify the same or similar status of the respective resource or service, thereby enabling an arrangement where each set of audio files represents are different 'theme'. The pre-selection of a set of audio files may be carried out as a user selection (received via the user interface of the computing device 130). In case only a single set of audio signals is available, this set can be considered to be a (n automatically) pre-selected set of audio signals. In the following description, the selection of an audio signal (for generation of the sound signal) refers to selection of an audio signal from the pre-selected set of audio signals.

In case the sound data for a certain resource type in the accessory sound database in the server device 150 includes multiple sets of audio files, the sound data received at the computing device 130 may include either only the pre-selected set of audio signals or it may comprise all sets of audio signals. In the former scenario the pre-selection is carried out in the computing device before requesting the sound data from the server 150, the sound data request specifies the set of audio signals to be delivered to the computing device and the server device 150 transmits only the pre-selected set of audio signals to the computing device 130, while in the latter scenario the server device 150 transmits all sets of audio signals to the computing device 130, which subsequently carries out the pre-selection.

Each of these audio signals may be provided as a digital audio signal. An audio signal may comprise, for example, uncompressed digital audio such as 16-bit or 24-bit pulse-code modulation (PCM) signal or an audio signal that is encoded using a predefined audio coding format known in the art, such as G.711, MP3 or AAC. In a further example, an audio signal may comprise rules for playing a sound or parameters that define the sound, such as rules according to the MIDI standard known in the art. An audio signal may be provided e.g. as a respective audio file, and the accessory sound database may store the audio file or it may include a link to the audio file stored elsewhere. The accessory sound control data that defines use of the audio signals of the corresponding accessory sound data may comprise one or more rules that define the usage of the audio signals in dependence of resource values received from the accessory device 110-*k*. In the following, a few non-limiting examples of arrangement of the accessory sound data and the accessory sound control data for one database entry are outlined.

In an example, the accessory sound data comprises a single audio signal and the accessory sound control data comprises information that defines playback frequency for the single audio signal in dependence of one or more resource values.

In another example, the accessory sound data comprises a plurality audio signals and the accessory sound control data comprises information that defines a selection rule for selecting one of the plurality of audio signals for playback in dependence of the one or more resource values.

In a further example, the accessory sound data comprises a plurality of audio signals and the accessory sound control data comprises the selection rule for selecting one of the plurality of audio signals for playback in dependence of one or more resource values and information that defines playback frequency for the selected audio signal in dependence of one or more resource values.

In a further example, the accessory sound data comprises either a single audio signal or a plurality of audio signals, and the accessory sound control data comprises first volume control information that defines (relative) volume for playback of the audio signal (selected e.g. according to one of the previous examples) in dependence of one or more resource value. The first volume control information may define, for example, that a higher volume is set in case one or more resource values indicate a value that exceeds a first predefined threshold and a lower (or normal) volume is set in case one or more resource values indicate a value that does not exceed the first predefined threshold. As another example, alternatively or additionally, the first volume control information may define that a higher volume is set in case one or more resource values indicate a value that is smaller than a second predefined threshold and that a lower (or normal) volume is set in case one or more resource values indicate a value that is larger than or equal to the second predefined threshold. Such volume control information may be employed, for example, to cause generation of a louder sound signal in response to resource values that are outside (or within) a predefined value range in comparison to the sound signal generated in response to resource values that are within (or outside) the predefined value range.

In a further example, the accessory sound data comprises either a single audio signal or a plurality of audio signals, and the accessory sound control data comprises second volume control information that defines (relative) volume for playback of the audio signal (selected e.g. according to one of the previous examples) in dependence of an estimated distance between the computing device 130 and the accessory device 110-$k$. The second volume control information may define setting the volume in dependence of a RSSI computed on basis of signal(s) that carry resource data response message(s) including respective resource values. As an example, such volume setting may include setting a higher volume in response to the RSSI exceeding a predefined threshold and setting a lower volume in response to the RSSI being smaller than or equal to the predefined threshold. Such volume control information may be employed, for example, to generate a louder sound signal for accessory devices 110 that are in close proximity to the computing device in comparison to the sound signals generated for accessory devices 110 that are further away.

In the above examples where a plurality of audio signals are defined or provided for a database entry of the accessory sound database, the plurality of audio signals may comprise, for example, audio signals that are different in audio content or audio signals that exhibit similar content at different volumes (e.g. at different signal levels). The accessory sound data and the respective accessory sound control data are defined separately for a number of resource types using respective database entries. Moreover, the accessory sound data and the respective accessory sound control data are typically different for different resource types.

Hence, in context of the examples outlined in the foregoing, generating the sound signal that is descriptive of resource values received from the accessory device 110-$k$ in the audio processing means 142 may comprise selecting an audio signal for the accessory device 110-$k$ from the local accessory sound database in dependence of one or more resource values received from the accessory device 110-$k$ and possibly processing the selected audio signal in dependence of one or more resource values received from the accessory device 110-$k$. The selection may be carried out in accordance with the selection rule that may be included in the accessory sound control data, whereas the processing may be carried out in accordance with a processing rule that may be included in the accessory sound control data. In this regard, the accessory sound control data may include a first processing rule that constitutes the first volume control information and/or a second processing rule that constitutes the second volume control information. The computing device 130 may identify the applicable database entry of the local accessory sound database by searching the local accessory sound database to identify the database entry that stores the respective resource type identifier.

Selection of an audio signal may comprise either selecting the only audio signal available in the accessory sound data of the identified database entry or selecting, according to the selection rule, one of the audio signals available in the accessory sound data of the identified database entry. Selection of the audio signal and/or processing of the audio signal may be carried out in dependence of a single resource value received from the accessory device 110-$k$ or in dependence of a sub-series of the time series of resource values received from the accessory device 110-$k$. Herein, any selection or processing in dependence the single resource value may comprise e.g. a selection or processing in dependence of the most recent resource value received from the accessory device 110-$k$, whereas selection or processing in dependence of the sub-series of resource values may comprise e.g. a selection or processing on basis of a representative resource value, which may be e.g. an average value, a maximum value or a minimum value of a predefined number of most recent resource values received from the accessory device 110-$k$, or another value derived on basis of the predefined number of most recent resource values received from the accessory device 110-$k$.

In case the audio signals in the local accessory sound database are provided as respective audio signals that are encoded using a predefined audio coding format, the audio processing means 142 may further decode the selected audio signal using the respective audio decoder into respective uncompressed digital audio signal prior to provision of the audio signal as the sound signal for the audio output means 144 and prior to any further audio processing that is to be applied to the selected audio signal before provision for playback by the audio output means 144.

As an example, processing an audio signal may comprise composing a processed audio signal in which the selected audio signal is repeated at a rate of frequency defined in dependence of one or more resource values and using the composed processed audio signal in the sound signal provided for playback in the audio output means 144. In this regard, the accessory sound control data for the respective resource type may include a third processing rule that defines a repetition rate for the selected audio signal in dependence of one or more resource values. Processing according to the third processing rule may hence comprise, for example, selecting or computing a repetition rate in dependence of one or more resource values received from the accessory device 110-$k$ and composing the processed audio signal where the selected audio signal is repeated in accordance with the selected or computed repetition rate.

Processing an audio signal may comprise scaling the audio signal in order to provide a processed audio signal at a desired (relative) volume level. The scaling may comprise selecting or computing a first scaling factor in dependence of one or more resource values and scaling the audio signal using the selected or computed first scaling factor. The selection or computation of the first scaling factor may be carried out e.g. in accordance with the first processing rule that may be included in the accessory sound control data. As examples in this regard, the first processing rule may define or compute the first scaling factor as a function of one or more resource values, and the scaling may be implemented by multiplying each sample value of the selected audio signal by the first scaling factor to derive a respective sample value of the processed audio signal. The processed audio signal may be provided as the sound signal to the audio output means 144.

As a particular example of computing the first scaling factor, the first scaling factor may be assigned a first value (a high value, e.g. 0.7) in response to a representative resource value this is descriptive of the current status of the resource value available in the accessory 110-$k$ exceeding a first predetermined threshold and the first scaling factor may be assigned a second value (a low value, e.g. 0.2) in response to said representative resource value being smaller than or equal to the first predetermined threshold value. As another example in this regard, the first scaling factor may be assigned the first value in response to the representative resource value being smaller than or equal to a second predetermined threshold and the first scaling factor may be assigned the second value in response to the representative resource value exceeding the second predetermined threshold value. Herein, the representative resource value may comprise, for example, the most recent resource value received from the accessory device 110-$k$, an average of a predefined number of most recent resource values received from the accessory device 110-$k$, the maximum of a predefined number of most recent resource values received from the accessory device 110-$k$, the minimum of a predefined number of most recent resource values received from the accessory device 110-$k$, etc. As a further example, the representative resource value may be computed on basis of a predefined number of most recent resource values using a predefined algorithm.

Along similar lines, the second processing rule that may be included in the accessory sound control data may define or compute the second scaling factor as a function of (estimated) distance between the computing device 130 and the accessory device 110-$k$, and the scaling may be implemented by multiplying each sample value of the selected audio signal by the second scaling value to derive a respective sample value of the processed audio signal. As an example in this regard, the setting of the second scaling factor may consider the distance in view of the RSSI computed on basis of signal(s) that carry one or more most recently received resource data response message(s) from the accessory device 110-$k$. As a particular example of scaling in dependence of the computed RSSI, the second scaling factor may be assigned a first value (a high value, e.g. 0.7) in response to the RSSI exceeding a predefined threshold and assigned a second value (a low value, e.g. 0.2) in response to the RSSI being smaller than or equal to the predefined threshold. As another example, a plurality of predefined thresholds may be defined, each having a respective predefined scaling factor value associated therewith such that a higher threshold value implies a higher second scaling value, and the second scaling factor may be assigned the predefined scaling value associated with highest of the thresholds that is smaller than the RSSI value.

In other examples, a distance indication that is based on a distance measure other than one based on RSSI, the estimated distance between the computing device 130 and the accessory device 110-$k$ may be computed on basis of respective position indications obtained for the computing device 130 and for the accessory device 110-$k$. The position indications may be obtained from respective positioning means in the computing device 130 and the accessory device 110-$k$ (the position indication for the accessory device 110-$k$ may be e.g. received in a resource discovery message or a resource data response message originating from the accessory device 110-$k$). A positioning means may comprise e.g. a satellite positioning means (such as GPS or Glonass) or a triangulation based positioning means as known in the art. Alternatively, the position indications in the computing device 130 and/or the accessory device 110-$k$ may be based on position data received as user input via the user interface of the respective device 130, 110-$k$.

In a further example, both the first and second processing rules may be employed, e.g. in a manner described in the foregoing, and the scaling factor for multiplying the sample values of the selected audio signal is derived as a combination of the first and second scaling factors, e.g. as a product of the first and second scaling factors.

The steps from 602 to 606 are typically carried out once for each accessory device 110 of interest, whereas the steps from 608 to 612 are carried out repeatedly when the computing device 130 is operational in generating the sound signal that is descriptive of the status of the accessory device 110-$k$ of interest. While the steps from 602 to 612 of the example described in the foregoing primarily concern discovery of a single accessory device 110-$k$ of interest and acquisition and usage of the accessory sound information for the single accessory device 110-$k$, this example readily generalizes into discovery of a plurality of accessory devices 110 of interest, acquisition of respective sound information for the plurality accessory devices 110 of interest and generating a composite sound signal that is descriptive of the current statuses of the resources or services available in or via plurality of discovered accessory devices 110 of interest.

In this regard, the presence of each of the plurality of accessory devices 110 of interest may be discovered and the associated accessory sound information may be acquired along the lines described in the foregoing in steps 602 to 606. Furthermore, the steps 608 and 610 are repeatedly carried out with each of the accessory devices 110 concerned to continuously obtain respective resource values for selection and/or processing of the respective audio signals. In this regard, for each of the plurality of accessory devices 110, a respective audio signal may be first selected, e.g. by using a procedure described in the foregoing, and the audio signals so obtained are combined (e.g. summed or averaged) in the composite sound signal for provision to the audio output means 144 in step 612. In the following, to facilitate editorial clarity of description, samples of the audio signal selected to represent current status of an accessory device 110-$j$ are denoted as $S_j$ and a scaling factor possibly to be used for scaling the selected audio signal $S_j$ is denoted as $f_j$.

In one example, no scaling is carried out in the audio processing means 142 in combining the audio signals and, assuming J accessory devices 110 of interest, samples of the composite audio signal may be derived e.g. by summing respective samples from each of the selected audio signals as $$S = \sum_{j=1}^{J} S_j$$

or by averaging respective samples from each of the selected audio signals as $$S = \frac{1}{J} \sum_{j=1}^{J} S_j.$$

If, for a given sample of the composite sound signal, there is no corresponding sample in one or more of the selected audio signals $S_j$, the missing sample may be replaced by a zero value or by some other suitable predefined sample value.

In another example, the audio processing means 142 employs scaling using respective scaling factors $f_j$ and hence derives samples of the composite sound signal as a linear combination of respective samples from each of the selected audio signals e.g. as $$S = \sum_{j=1}^{J} f_j S_j \text{ or } S = \frac{1}{J} \sum_{j=1}^{J} f_j S_j.$$

If, for a given sample of the composite sound signal, there is no corresponding sample in one or more of the selected audio signals $S_j$, the missing sample may be replaced by a zero value or by some other suitable predefined sample value. Each of the scaling factors $f_j$ may comprise, for example, the first scaling factor derived for the respective accessory devices 110-$j$, the second scaling factor derived for the respective accessory devices 110-$j$ or the product of the first and second scaling factors derived for the respective accessory devices 110-$j$.

Figure 7:
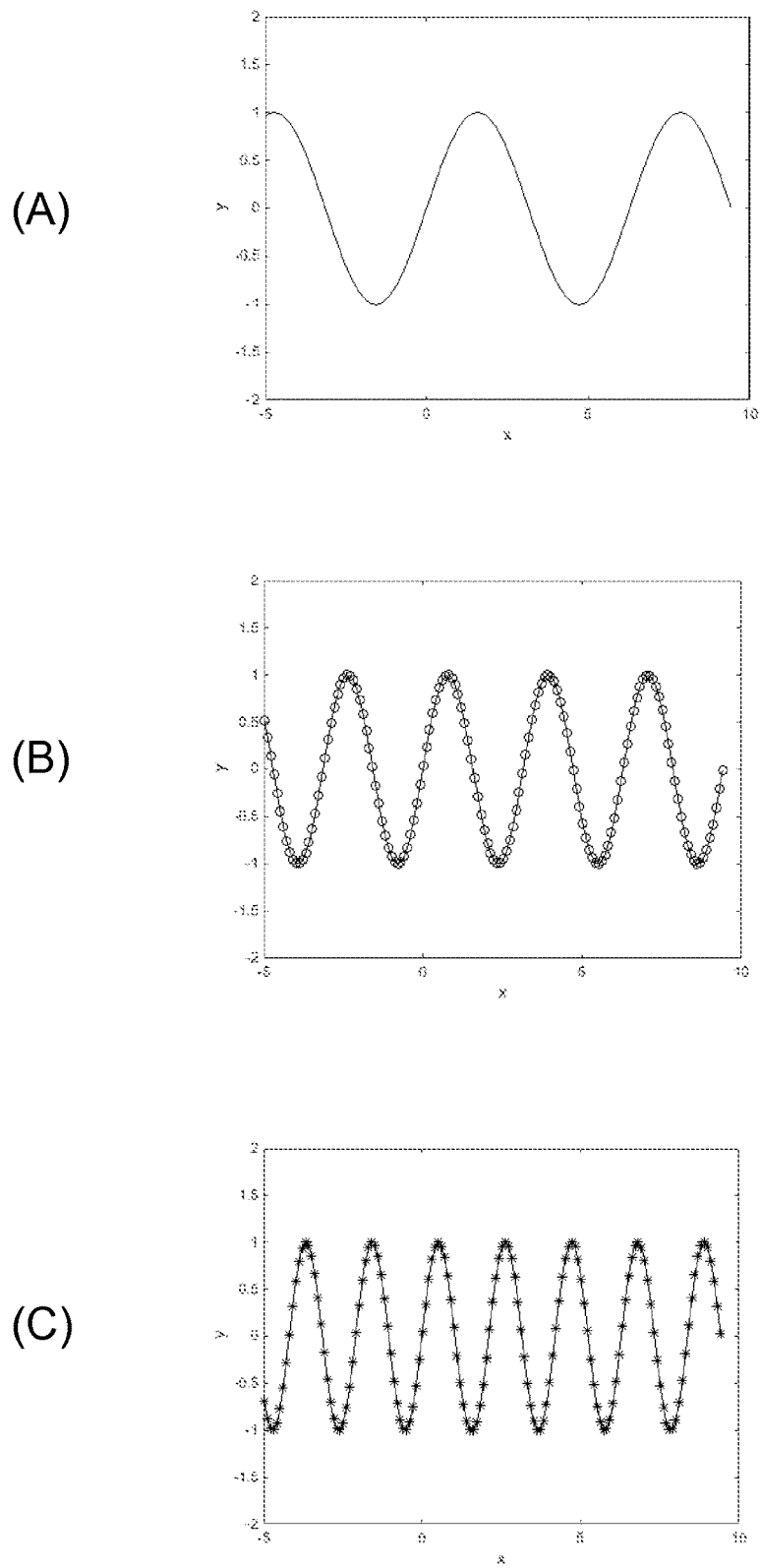
FIG. 7 depicts exemplifying audio signals in accordance with an example embodiment.
Figure 8:
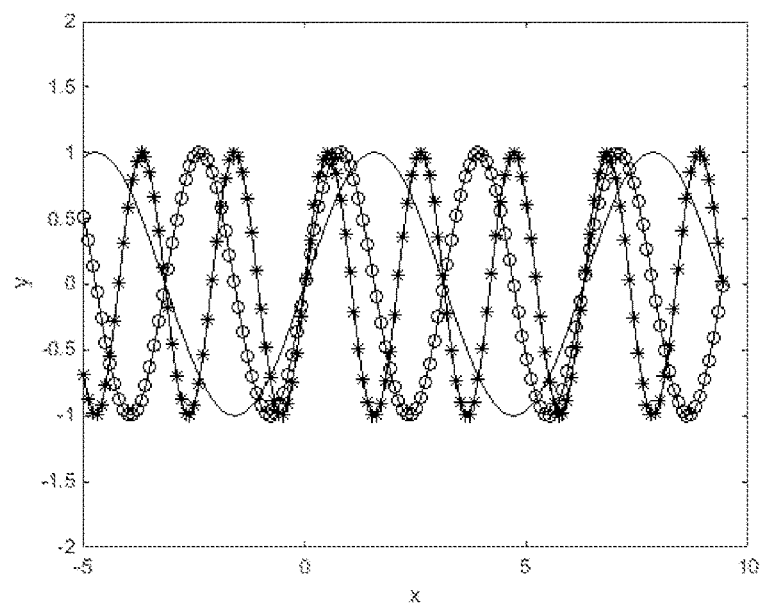
FIG. 8 depicts exemplifying audio signals and an exemplifying sound signal in accordance with an example embodiment.
Figure 8:
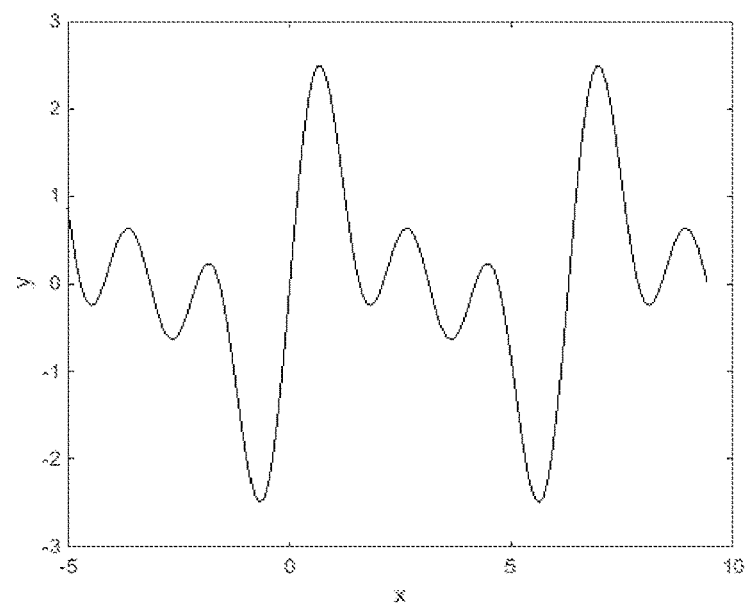
Figure 9:
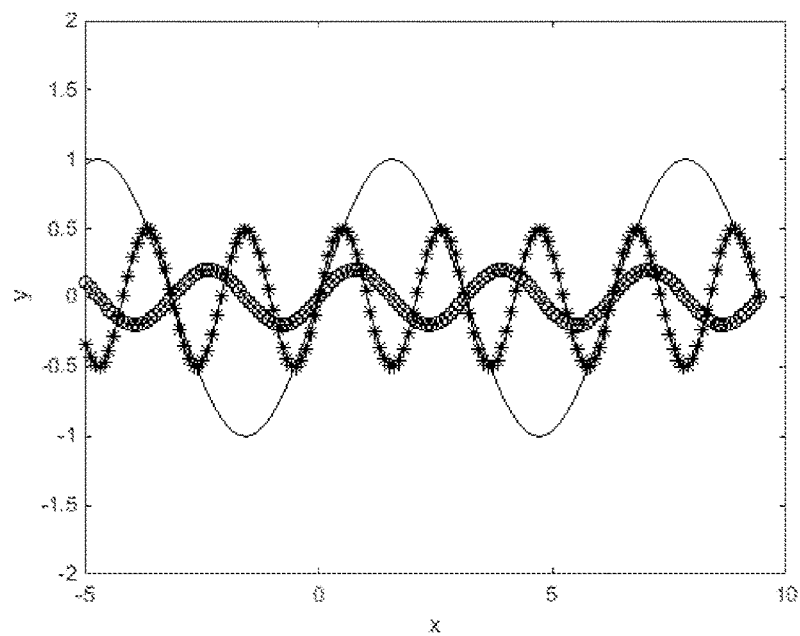
FIG. 9 depicts exemplifying processed audio signals and an exemplifying sound signal in accordance with an example embodiment.
Figure 9:
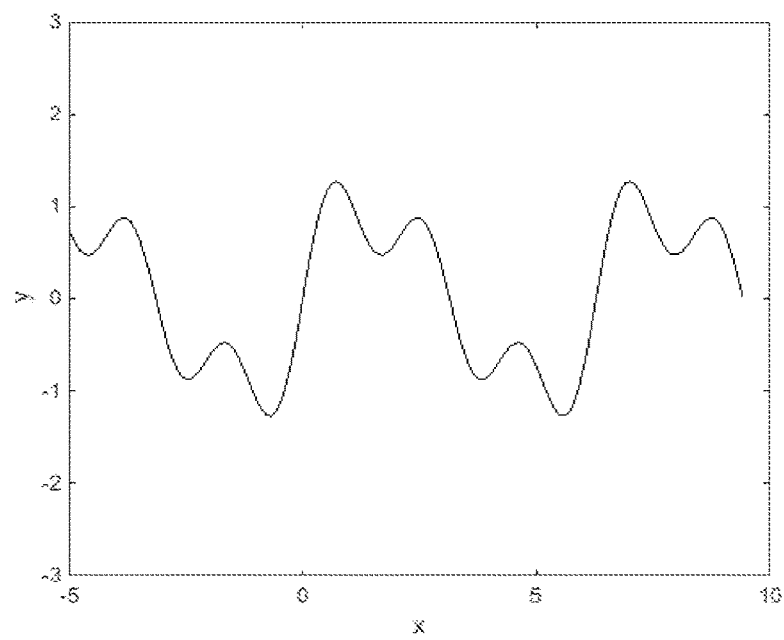

FIGS. 7 to 9 provide an example of selected audio signals, respective processed audio signal signals, and corresponding composite sound signals. In FIGS. 7 to 9, the x axis represents time and y axis represents amplitude of a signal. In FIG. 7, illustration A depicts a first audio signal, illustration B depicts a second audio signal and illustration C depicts a third audio signal. To facilitate telling the first, second and third audio signals apart in illustrations of FIG. 8, the first audio signal is depicted using a curve without markers, the second audio signal is depicted using a curve with circular markers and the third audio signal is depicted using a curve with asterisk-like markers. Herein, the first, second and third audio signals are depicted as respective sinewaves at different frequencies. This is, however, a choice made for graphical clarity of illustrations of FIGS. 7 and 8, and the audio signals of the accessory sound database are typically more complex in content.

FIG. 8 depicts, in illustration D, the first, second and third audio signals overlaid in a single graph, whereas illustration E depicts the sound signal derived as a combination of the first, second and third audio signals, which in this example involves a sum of these three signals. Illustration F in FIG. 9 depicts processed first, second, and third audio signals, scaled using the respective scaling factors. In this example, scaling factor applied to the first audio signal is $f_1=1$, scaling factor applied to the second audio signal is $f_2=0.2$, and scaling factor applied to the third audio signal is $f_3=0.5$. Illustration G in FIG. 9 further depicts the sound signal derived as a combination of the processed first, second and third audio signals, which in this example involves a sum of the first, second and third processed audio signals of the illustration F.

In a further example, the selected audio signals $S_j$ are combined into the composite sound signal such that the exhibit a spatial audio image that reflects the relative positions of the accessory devices 110-$j$ in relation to the computing device 130. In other words, each of the selected audio signals $S_j$ is rendered as a respective directional audio signal that occupies a respective spatial position in a spatial audio image represented by the composite sound signal. For such a scenario, the computing device 130 has knowledge or estimate of its own position with respect to positions of the considered accessory devices 110-$j$, e.g. its own geographical position and respective geographical positions of the considered accessory devices 110-$j$. Furthermore, the computing device 130 may determine its orientation with respect to the considered accessory device 110-$j$, and combine the selected audio signals $S_j$ into respective spatial positions of the audio image that reflect their geographical position with respect to the current geographical position and orientation of the computing device 130.

The current geographical position of an accessory device 110-$j$ may be obtained, for example, by receiving an indication in this regard in resource value response messages from the respective accessory device 110-$j$. As another example, the wireless communication apparatus 132a employed to receive the resource value response messages from the accessory devices 110-$j$ may comprise a directional antenna, which may provide an indication of the direction of arrival that serves as directional information with respect to the current geographical position of the respective accessory device 110-$j$.

The orientation of the computing device 130 (or a user thereof) with respect to the respective positions of one or more of the considered accessory devices 110-$j$ may be obtained using any suitable method known in the art. As an example in this regard, the approaches described in section 2.4 of the publication Mikko Peltola, "*Augmented Reality Audio Applications in Outdoor Use*", M.Sc. thesis, Helsinki University of Technology, 2009 (available on filing date of the present application e.g. at http://lib.tkk.fi/Dipl/2009/urn100054.pdf).

In an example, in addition to providing the (composite) sound signal via the audio output means 144, the computing device 130 may further display the resource values received from the accessory device 110-$j$ via the user interface of the computing device 130. In this regard the displayed information, for each considered accessory device 110-$j$, may involve one or more most recent resource values received from the accessory device 110-$j$ or a value derived on basis of one or more most recent resource values received from the accessory device 110-$j$ together with one or more of the accessory device identifier received from the accessory device 110-$j$ and a textual description of the resource type provided by or via the accessory device 110-$j$ Consequently, a user viewing the displayed information is likely able to associate at least some of the displayed pieces of information with devices in his/her vicinity and, hence, recognize respective audio signals included in the sound signal played back by the audio output means 144 to the respective devices in his/her vicinity.

In another example, the computing device 130 may (further) increase the volume of the audio signal representing a considered accessory device 110-$j$ that is in close proximity to the computing device to provide a user of the computing device 130 an indication of the accessory device 110 that serves as the source of the resource values that control generation of the respective audio signal. As an example in this regard, the audio processing means 142 employ a further scaling factor with a predefined value higher than 1 (e.g. in a range from 1.1. to 1.5) in scaling of samples of the audio signal that reflects the resource values originating from the accessory device 110-$j$ in response to the RSSI computed on basis of signal(s) that carry resource data response message(s) originating from the accessory device 110-$j$ exceeding a predefined threshold that is considered as an indication of the computing device 130 being in immediate vicinity of the accessory device 110-$j$. As a variation of this example, instead of applying the further scaling factor, the RSSI exceeding the predefined threshold may result in the audio processing means 142 further introducing an audible indication in the sound signal provided for playback in the audio output means 144. Such audible indication may comprise e.g. a predefined alarm sound or recitation of the accessory device identifier associated with the accessory device 110-$j$, generated in the audio processing means 142 by using a voice synthesis technique known in the art.

Figure 10:
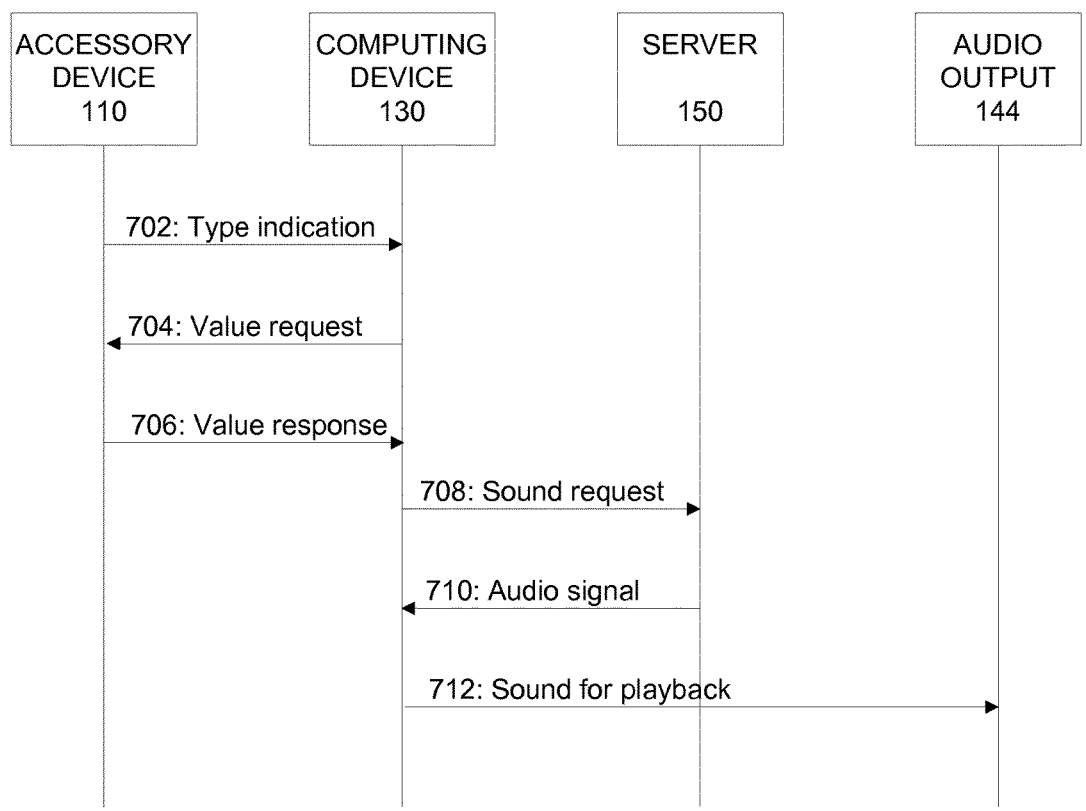
FIG. 10 depicts an example of signaling between elements of the communication arrangement according to an example embodiment.

FIG. 10 depicts a signaling chart that serves as another example of operation of the communication arrangement 100 at a high level. The signaling chart of FIG. 10 is a variation of that illustrated in FIG. 6 and described in detail in the foregoing. In the example of FIG. 10, step 702 may be carried out in a manner described in context of step 602 in the foregoing, while steps 704 and 706 may be carried out in manner described in the foregoing for steps 608 and 610, respectively.

A major difference between the operation according to the signaling chart of FIG. 10 in comparison to that according to FIG. 6 is that the accessory sound request of step 708 includes, in addition to the resource type identification transmitted in the accessory sound request of step 604, one or more resource values received at the computing device 130 from the respective accessory device 110. Also in this scenario the server device 150 searches the accessory sound database to identify the database entry pertaining to the resource type indicated in the accessory sound request received from the computing device 130, but instead of transmitting the accessory sound data and the accessory sound control data to the computing device 130, the server device 150 uses the pieces of data to select the audio signal for the requested resource type and to process (e.g. scale) the selected audio signal according. The selection and processing of the audio signal may be carried out in the server 150 as described in the foregoing for the corresponding operations in the audio processing means 142. In step 710, the server device 150 transmits the selected, and possibly processed, audio signal to the computing device 130.

The computing device 130 may carry out the procedures pertaining to steps 702 to 706 with a plurality of accessory devices 110-j of interest, and the computing device 130 may request the corresponding audio signal from the server device 150 for the plurality of accessory devices 110-j of interest. The audio processing means 142 may generate the sound signal for provision to the audio output means 144 for playback in step 712 on basis of the audio signal received from the server device 150 for a single accessory device 110 or the audio processing means 142 may generate the composite sound signal for provision to the audio output means 144 on basis of the plurality of audio signals received from the server device 150 for the respective plurality of accessory devices 110. Also in this scenario the generation of the (composite) sound signal may follow the examples described in the foregoing for generating the (composite) sound signal on basis of audio signals selected in the computing device 130.

FIG. 11 depicts a flowchart that outlines a method 200 according to an example embodiment of the invention. The method 200 may be carried out in an apparatus, e.g. in the computing device 130 described in the foregoing. The method 200 comprises storing respective sound information for one or more resource types, as indicated in block 210. As described in the foregoing, the sound information may be stored in database entries of the accessory sound information database, and/or the sound information for a resource type may comprise sound data that defines one or more audio signals associated with the resource type and sound control data that defines use of the sound data for generation of a sound signal that is descriptive of a status of a resource that represents said resource type in dependence of one or more resource values that indicate the status of the resource.

The method 200 further comprises receiving, from one or more accessory devices 110, a respective time series of resource values that indicates a status of a resource available in the respective accessory device 110, as indicated in block 220 and generating, in dependence of resource values in said one or more time series, using said sound information for the resource types available in said one or more accessory devices 110, a sound signal that is descriptive of the statuses of said resources available in said one or more accessory devices 110, as indicated in block 230.

The method 200, may be varied in a number of ways, e.g. in accordance with the description of the operation of the computing device 130 in accordance with the exemplifying signaling charts of FIGS. 6 and 10.

Referring back to components of the accessory device 110, the computing device 130 and the server device 150, the processor 116, 136, 156 is configured to read from and write to the respective memory 115, 135, 155. Although each of the processors 116, 136, 156 is depicted as a respective single component, any of the processors 116, 136, 156 may be implemented as respective one or more separate processing components. Similarly, although each of the memories 115, 135, 155 is depicted as a respective single component, any of the memories 115, 135, 155 may be implemented as respective one or more separate components, some or all of which may be integrated/removable and/or may provide permanent/semi-permanent/dynamic/cached storage.

The memory 115, 135, 155 may store the respective computer program comprising computer-executable instructions that control the operation of the respective device 110, 130, 150 when loaded into the respective processor 116, 136, 156. As an example, the computer program may include one or more sequences of one or more instructions. The computer program may be provided as a computer program code 137. The processor 136 is able to load and execute the computer program by reading the one or more sequences of one or more instructions included therein from the memory 135. The one or more sequences of one or more instructions may be configured to, when executed by the processor 136, cause the computing device 130 to carry out operations, procedures and/or functions described in the foregoing in context of the communication arrangement 100. Hence, the computing device 130 may comprise at least one processor 136 and at least one memory 135 including computer program code 137 for one or more programs, the at least one memory 135 and the computer program code 137 configured to, with the at least one processor 136, cause the computing device 130 to perform operations, procedures and/or functions described in the foregoing in context of the computing device 130. Similar considerations are equally valid for corresponding components 11x of the accessory device 110 and for corresponding components 15x of the server device 150.

The computer programs stored in any of the memories 115, 135, 155 may be provided e.g. as a respective computer program product comprising at least one computer-readable non-transitory medium having the respective computer program code 117, 137, 157 stored thereon, the computer program code, when executed by the respective device 110, 130, 150, causes the apparatus 110, 130, 150 at least to perform operations, procedures and/or functions described in the foregoing in context of the respective device 110, 130, 150 in description of operation of the communication arrangement 100. The computer-readable non-transitory medium may comprise a memory device or a record medium such as a CD-ROM, a DVD, a Blu-ray disc or another article of manufacture that tangibly embodies the computer program. As another example, the computer program may be provided as a signal configured to reliably transfer the computer program.

Reference(s) to a processor should not be understood to encompass only programmable processors, but also dedicated circuits such as field-programmable gate arrays (FPGA), application specific circuits (ASIC), signal processors, etc. Features described in the preceding description may be used in combinations other than the combinations explicitly described.

Although functions have been described with reference to certain features, those functions may be performable by other features whether described or not. Although features have been described with reference to certain embodiments, those features may also be present in other embodiments whether described or not.

The invention claimed is:

1. An apparatus comprising
at least one processor; and
at least one memory including computer program code;
the at least one memory and the computer program code configured to, with the at least one processor, cause the apparatus at least to perform:
transmit, for one or more accessory devices, from the apparatus to a server device, a sound request comprising a resource type identifier to request sound information for the resource type identified by the respective resource type identifier;
receive, from the server device, respective sound information for one or more resource types, the sound information for a resource type comprising:
sound data that defines one or more audio signals associated with the resource type, and
sound control data that defines use of the sound data for generation of a sound signal that is descriptive of a status of a resource that represents said resource type dependent on one or more resource values that indicate the status of the resource;
receive, using said apparatus, a respective time series of resource values that indicates a status of a resource available in at least one respective accessory device of the one or more accessory devices; and
generate, dependent on resource values in said one or more time series, using said sound information for the resource types available in said one or more accessory devices, the sound signal that is descriptive of the statuses of said resources available in said one or more accessory devices.

2. An apparatus according to claim 1, wherein the at least one memory and the computer program code are further configured to, with the at least one processor, cause the apparatus at least to perform:
receive, from said one or more accessory devices over a respective wireless link, one or more resource discovery messages that comprise the resource type identifier that identifies the resource available in the at least one respective accessory device.

3. An apparatus according to claim 1, wherein a resource value comprises a measurement value from a sensor that is arranged to measure at least one of the following:
a predefined environmental characteristic, or
a predefined vital sign of a person or an animal.

4. An apparatus according to claim 1, wherein said sound control data comprises a selection rule for selecting an audio signal from the sound data dependent on one or more resource values, and wherein generating the sound signal comprises:
identify stored sound data and sound control data for the resource type available in a first accessory device of said one or more accessory devices, and
use the selection rule of the identified sound control data to select an audio signal from the identified sound data dependent on one or more resource values of the time series of resource values received from said first accessory device.

5. An apparatus according to claim 1, wherein said sound control data comprises a first processing rule for processing an audio signal dependent on one or more resource values, and wherein generating the sound signal comprises:
identify stored sound data and sound control data for the resource type available in a first accessory device of said one or more accessory devices, and
process an audio signal of the identified sound data according to the first processing rule of the identified sound control data dependent on one or more resource values of the time series of resource values received from said first accessory device.

6. An apparatus according to claim 5, wherein said processing comprises:
selecting a first scaling factor dependent on said one or more resource values in accordance with said first processing rule, and
scaling the audio signal using the first scaling factor.

7. An apparatus according to claim 5, wherein said processing comprises:
selecting a repetition rate dependent on said one or more resource values in accordance with said first processing rule, and
repeating the audio signal in accordance with said repetition rate.

8. An apparatus according to claim 4, wherein said selection or processing is carried out dependent on at least one of the following:
the most recent resource value received from the first accessory device, and
a representative resource value computed on basis of a predefined number of most recent resource values received from the first accessory device.

9. An apparatus according to claim 1, wherein said sound control data comprises a second processing rule for processing an audio signal from the sound data in dependent on a distance between the apparatus and a first accessory device, and wherein generating the sound signal comprises:
identifying stored sound data and sound control data for the resource type available in a first accessory device of said one or more accessory devices, and
processing an audio signal of the identified sound data according to the second processing rule of the identified sound control data dependent on one or more resource values of the time series of resource values received from said first accessory device.

10. An apparatus according to claim 9,
wherein receiving the time series of resource values comprises receiving, from said first accessory device, over a wireless link, one or more resource data response messages that comprise said resource values, and wherein said processing comprises:
deriving a received signal strength indicator, RSSI, that is descriptive of the signal strength of said one or more resource data response messages,
deriving a second scaling factor dependent on the derived RSSI, and
scaling the audio signal using the second scaling factor.

11. An apparatus according to claim 1, wherein generating the sound signal comprises:
determining whether the apparatus is in close proximity to a first accessory device of said one or more accessory devices, and
including in the sound signal a predefined audible indication in response to determining that the apparatus in close proximity to said first accessory device.

12. An apparatus according to claim 11,
wherein receiving the time series of resource values comprises receiving, from said first accessory device, over a wireless link, one or more resource data response messages that comprise said resource values, and wherein said determining comprises:
deriving a received signal strength indicator, RSSI, that is descriptive of the signal strength of said one or more resource data response messages; and
determining the first apparatus to be in close proximity to said first accessory device in response to the derived RSSI exceeding a predetermined threshold.

13. An apparatus according to claim 1,
wherein the at least one memory and the computer program code are further configured to cause the apparatus to determine the position and orientation of the apparatus with respect to a position of a first accessory device of said one or more accessory devices, and wherein generating the sound signal comprises:
generating a spatial audio image where the spatial position of the audio signal that is descriptive of the status of the resources available in said first accessory device reflects the position of said first accessory device with respect to the apparatus.

14. An apparatus according to claim 1, further comprising a respective audio signal for each of said one or more accessory devices dependent on resource values received in respective the one or more time series; and
combine said respective audio signal for each of said one or more accessory devices into the sound signal.

15. An apparatus according to claim 1, wherein said apparatus is arranged to communicate with other apparatuses using Bluetooth® Low Energy standard.

16. A method comprising:
transmitting, for one or more accessory devices, from an apparatus to a server device, a sound request comprising a resource type identifier to request sound information for the resource type identified by the respective resource type identifier;
receive, from the server device, respective sound information for one or more resource types, the sound information for a resource type comprising
sound data that defines one or more audio signals associated with the resource type, and
sound control data that defines use of the sound data for generation of a sound signal that is descriptive of a status of a resource that represents said resource type dependent on one or more resource values that indicate the status of the resource;
receiving, in the apparatus, a respective time series of resource values that indicates a status of a resource available in at least one respective accessory device of the one or more accessory devices; and
generating, in the apparatus, dependent on resource values in said one or more time series, using said sound information for the resource types available in said one or more accessory devices, the sound signal that is descriptive of the statuses of said resources available in said one or more accessory devices.

17. A method according to claim 16, further comprising:
receiving, in the apparatus from said one or more accessory devices over a respective wireless link, one or more resource discovery messages that comprise the resource type identifier that identifies the resource available in the at least one respective accessory device.

18. A method according to claim 16, wherein a resource value comprises a measurement value from a sensor that is arranged to measure at least one of the following:
a predefined environmental characteristic, or
a predefined vital sign of a person or an animal.

19. A method according to claim 16, wherein said sound control data comprises a selection rule for selecting an audio signal from the sound data dependent on one or more resource values,
wherein the method comprises identifying stored sound data and sound control data for the resource type available in a first accessory device of said one or more accessory devices, and
wherein generating the sound signal comprises using the selection rule of the identified sound control data to select an audio signal from the identified sound data dependent on one or more resource values of the time series of resource values received from said first accessory device.

20. A non-transitory computer readable medium comprising program instructions stored thereon to perform at least the following:
transmit, for one or more accessory devices, from an apparatus to a server device, a sound request comprising a resource type identifier to request sound information for the resource type identified by the respective resource type identifier;
receive, from the server device, respective sound information for one or more resource types, the sound information for a resource type comprising sound data that defines one or more audio signals associated with the resource type, and sound control data that defines use of the sound data for generation of a sound signal that is descriptive of a status of a resource that represents said resource type dependent on one or more resource values that indicate the status of the resource;
receive, in the apparatus, from, a respective time series of resource values that indicates a status of a resource available in at least one respective accessory device; and
generate, dependent on resource values in said one or more time series, using said sound information for the resource types available in said one or more accessory devices, the sound signal that is descriptive of the statuses of said resources available in said one or more accessory devices.

* * * * *

UNITED STATES PATENT AND TRADEMARK OFFICE
CERTIFICATE OF CORRECTION

PATENT NO. : 10,269,231 B2
APPLICATION NO. : 15/763785
DATED : April 23, 2019
INVENTOR(S) : Teemu Savolainen Page 1 of 1

It is certified that error appears in the above-identified patent and that said Letters Patent is hereby corrected as shown below:

In the Claims

Column 28
Line 44, in Claim 20, "in the apparatus, from, a respective" should read --in the apparatus, a respective--

Signed and Sealed this
Third Day of December, 2019

Andrei Iancu
*Director of the United States Patent and Trademark Office*